United States Patent
Cassoni et al.

(10) Patent No.: US 8,413,789 B2
(45) Date of Patent: Apr. 9, 2013

(54) METHOD AND APPARATUS FOR ORIENTING ARTICLES

(75) Inventors: Robert Paul Cassoni, Washington, OH (US); Clifford Theodore Papsdorf, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/371,581

(22) Filed: Feb. 13, 2012

(65) Prior Publication Data

US 2012/0138425 A1 Jun. 7, 2012

Related U.S. Application Data

(63) Continuation of application No. 12/002,079, filed on Dec. 14, 2007, now Pat. No. 8,136,651.

(51) Int. Cl.
*B65G 47/14* (2006.01)

(52) U.S. Cl. .................. 198/397.01; 198/380; 198/393; 198/397.04; 198/397.06

(58) Field of Classification Search ....................... None
See application file for complete search history.

(56) References Cited

U.S. PATENT DOCUMENTS

| | | | | |
|---|---|---|---|---|
| 3,797,195 A | * | 3/1974 | Brink et al. | ...................... 53/471 |
| 4,610,345 A | * | 9/1986 | Spreen et al. | ................. 198/392 |
| 4,632,028 A | * | 12/1986 | Ackley | ............................. 101/40 |
| 4,664,248 A | | 5/1987 | Goodman, Jr. | |
| 4,709,798 A | | 12/1987 | Herzog | |
| 4,884,678 A | | 12/1989 | Graham | |
| 5,178,256 A | | 1/1993 | Anderson | |
| 5,314,055 A | | 5/1994 | Gordon | |
| 5,404,991 A | | 4/1995 | Nakamura | |
| 5,479,762 A | | 1/1996 | Bliss | |
| 5,484,052 A | | 1/1996 | Pawloski | |
| 5,564,551 A | * | 10/1996 | Schmitt | ........................ 198/392 |
| 5,836,243 A | | 11/1998 | Ackley | |
| 6,058,556 A | | 5/2000 | Jones | |
| 6,079,546 A | | 6/2000 | Marti Sala | |
| 6,176,369 B1 | | 1/2001 | Petrovic | |
| 6,209,708 B1 | | 4/2001 | Philipp | |
| 6,390,280 B1 | * | 5/2002 | Boyce | ........................... 198/540 |
| 7,262,335 B2 | | 8/2007 | Motsch | |
| 7,270,651 B2 | | 9/2007 | Adams | |
| 7,275,400 B2 | | 10/2007 | Severns | |

FOREIGN PATENT DOCUMENTS

| | | |
|---|---|---|
| DE | 2754189 A1 | 10/1979 |
| GB | 1355654 A | 6/1974 |
| JP | 11-139543 A | 5/1999 |
| JP | 11-157635 A | 6/1999 |
| JP | 2006-89093 A | 4/2006 |
| JP | 2006-160416 A | 6/2006 |

* cited by examiner

*Primary Examiner* — Kavel Singh
(74) *Attorney, Agent, or Firm* — James T. Fondriest

(57) ABSTRACT

A method for sorting and/or orienting caps using an automated capping line can comprise providing a single cap to a cap-receiving cavity defined in a body of a puck. In various embodiments, the body can be vibrated to settle and/or orient the cap to a properly oriented position within the cap-receiving cavity. In at least one embodiment, the vibrating can include applying horizontal vibration and/or vertical vibration to the body. As a result, the properly oriented caps can be conveyed to a capping machine configured to apply each cap to a cap-receiving portion of a container.

5 Claims, 13 Drawing Sheets

METHOD AND APPARATUS FOR ORIENTING ARTICLES

CROSS REFERENCE TO RELATED APPLICATION

This application is a continuation of prior U.S. application Ser. No. 12/002,079 filed Dec. 14, 2007 now U.S. Pat. No. 8,136,651.

FIELD OF THE INVENTION

The present invention relates to a method and apparatus for orienting articles, and more particularly relates to a method and apparatus for sorting and/or orienting caps for containers using an automated processing line.

BACKGROUND OF THE INVENTION

In the commercial processing of goods, it is common for the goods to be at least partially assembled and prepared for shipment using an automated processing line. In various embodiments, the automated processing line can include a machine configured to apply a cap to a product-filled container, to seal the container and prepare the container for shipment. In at least one embodiment, the machine can include a capping machine configured to place, snap, and/or screw the cap onto a cap-receiving portion of the container. For the automated processing line to run smoothly, the caps usually need to be sorted and/or oriented such that a single cap can engage the cap-receiving portion of the container when applied thereto. Various automated cap sorting and/or orienting processes are directed towards sorting and/or orienting the caps, however, most of these automated processes are overly complicated and can require many expensive components. Further, the current automated processes can have a tendency to cause the caps to jam and/or mis-orient with the processing line thereby causing an inefficient capping result. Additionally, in various embodiments, current capping processes can require costly and inefficient change-over procedures when the capping machine is switched from running a first cap, having a first size and geometry, and a second cap, having a second size and geometry. Additionally, none of the current automated capping processes teach in-cavity orienting of the caps. What is needed is an improvement over the foregoing.

SUMMARY OF THE INVENTION

In at least one general aspect, a method for sorting and/or orienting caps can comprise providing a single cap to a cap-receiving cavity defined in a body of a puck. In various embodiments, the body can be configured to receive vibrational energy to cause the cap to orient to a properly oriented position within the cap-receiving cavity. In at least one embodiment, the vibrational energy can include applying horizontal vibrational energy and/or vertical vibrational energy to the body, for example. As a result, the properly oriented caps can be conveyed to a capping machine configured to apply each cap to a cap-receiving portion of a container.

In at least one general aspect, a puck insert can comprise a body including a surface having a cap-receiving cavity defined therein. In various embodiments, the cap-receiving cavity can be configured to loosely receive a single cap. In at least one embodiment, the cap-receiving cavity can be configured to orient the cap to a properly oriented position when the body is agitated and/or vibrated. In various embodiments, the puck insert can be formed through the use of a mold where the mold can be generated from a computerized model of the mold. In at least one embodiment, the formed puck insert can be engaged with a puck carrier configured to be attached to a conveyor.

In at least one general aspect, a plurality of pucks can each include a cavity configured to receive a single cap. In various embodiments, a plurality of caps can be provided to at least a portion of the plurality of pucks. In at least one embodiment, the caps can be settled into at least some of the cavities in the portion of the plurality of pucks. In at least such an embodiment, the settled caps can be viewed to determine if the caps are oriented in a desired position or a non-desired position. In various embodiments, a first group of pucks having caps oriented in the desired position can be separated from a second group of pucks having caps oriented in the non-desired position.

BRIEF DESCRIPTION OF DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 1:
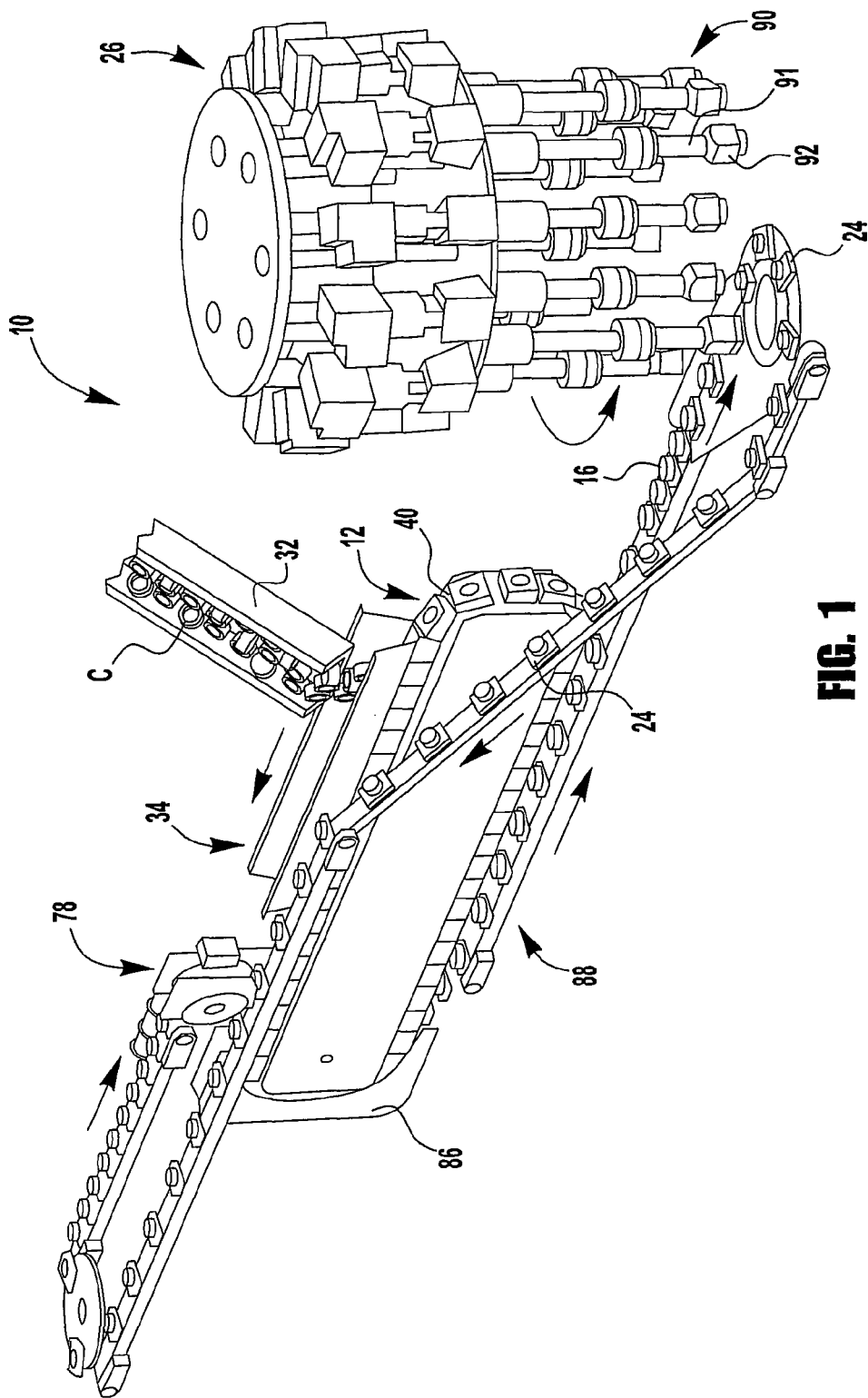
FIG. 1 is a perspective view of components configured for use with a method for cap sorting and/or orienting in accordance with one non-limiting embodiment of the present invention.

In various embodiments, referring to FIG. 1, a plurality of caps "C" can be sorted and/or oriented using an automated processing line 10. In at least one embodiment, a plurality of pucks 12 can be provided to a sort conveyor 14 of the automated processing line 10 where each puck 12 can be configured to receive a cap. In such an embodiment, the plurality of caps can be provided to the sort conveyor 14 and/or to at least a portion of the plurality of pucks 12 attached thereto. As a result, in various embodiments, a first group of caps 16 can be settled into at least some of a plurality of cavities 18 defined in top surfaces 20 of the portion of the plurality of pucks 12, and, a second group of caps, or "excess caps" 22, can remain on the top surfaces 20 of the portion of the plurality of pucks 12. In at least one embodiment, the excess caps 22 can be removed from the top surfaces 20 to leave only the first group of caps 16 within at least some of the cavities 18. In various embodiments, the portion of the plurality of pucks 12 can be vibrated to cause the first group of caps 16 to be sorted and settle and/or uniformly orient within at least some of the cavities 18. In at least one embodiment, cap carriers 24 can be dispensed to the top surfaces 20 of the pucks 12 containing the first group of uniformly oriented caps 16, to engage the uniformly oriented caps within the cavities 18. As a result, in such an embodiment, the first group uniformly oriented caps 16 can be transferred to the cap carriers 24 and conveyed to a capping machine 26. In various embodiments, the capping machine 26 can apply the first group of uniformly oriented caps 16 to cap-engaging portions of product-filled containers (not illustrated).

For purposes of this specification the term "caps" may comprise any cap, lid, and/or other suitable article configured to be engaged with a container to thereby seal the container. Examples of caps that can be used with the present invention are illustrated in FIGS. 16A-16E. In various embodiments, the caps can have any size and/or geometry suitable for engaging the containers. In at least one embodiment, the caps can each comprise a body portion and a product dispensing portion, such as a nozzle, for example. In various embodiments, the product-dispensing portion of the cap can include a flip-top portion moveable between an open position and a closed position. In such an embodiment, the product-dispensing portion can be configured to dispense product through the nozzle when in the open position, for example. In other various embodiments, the nozzle can be opened and closed using any other suitable member. In at least one embodiment, the body portion of the cap can include an outer shell defining an aperture therein. In such an embodiment, the outer shell and aperture can be engaged with the cap-engaging portion of the container by the capping machine in a snap-fit and/or press-fit fashion, for example. In other various embodiments, an inner wall of the outer shell can comprise threads to allow the capping machine to threadably engage the threads of the caps with threads on the cap-engaging portion of the containers.

As outlined above, in various embodiments, a plurality of caps can be provided to and sorted by the automated processing line 10. In at least one embodiment, referring to FIGS. 2 and 3, caps can be provided to a sorter 34 through the use of a feeder 28 comprising an elevator 30 and a feed chute 32. In such an embodiment, an operator and/or machine can feed the plurality of caps to the elevator 30. In various embodiments, the elevator 30 can be configured to convey the plurality of caps to the feed chute 32 at any suitable feed rate. In at least one embodiment, the feed rate can be proportional to the speed of a sort conveyor 14 of a sorter 34, for example. In further various embodiments, the feed rate of the plurality of caps can be dependent on the size, weight, and/or geometry of the caps being run through the automated processing line 10. In any case, if the elevator 30 is run at too high of a feed rate, too many caps can be delivered to the sorter 34, which can cause cap nesting within at least some of the cavities 18 of the sort conveyor 14. Conversely, if the elevator 30 is run at too low of a feed rate, too few caps can be delivered to the sorter 34, causing at least some empty cavities 18 in the sort conveyor 14.

Further to the above, in various embodiments, the elevator 30 can comprise a feed conveyor 36 operably connected with a sensor (not illustrated) where the sensor can be configured to view the level of caps within the feed chute 32 and/or a hopper (not illustrated) configured for use with the feed chute 32. In at least one embodiment, the sensor can include a position sensor and/or a height sensor, for example. In such an embodiment, the sensor can receive an input signal indicative of the cap level in the feed chute 32 and/or hopper and can then transmit an output signal to a receiver in communication with the elevator 30 and feed conveyor 36. In various embodiments, when the hopper and/or feed chute 32 is empty, the sensor can transmit an output signal to the receiver to cause the feed conveyor 36 to activate and feed caps. Conversely, when the hopper and/or feed chute 32 is filled with caps, the sensor can transmit an output signal to the receiver to cause the feed conveyor 36 to stop feeding the caps, for example. In other various embodiments, the feed conveyor 36 can be run constantly to continuously supply caps to the hopper and/or feed chute 32. In at least one embodiment, the feed conveyor 36 can include a feed belt configured to be movably situated around at least two rollers (not illustrated), for example. In at least one embodiment, at least one roller can be operably engaged with an actuator (not illustrated) configured to motivate the feed belt around the roller in any suitable direction and thereby motivate the plurality of caps towards the feed chute 32.

As described above, in various embodiments, the feed chute 32 can comprise a hopper (not illustrated) configured to house the plurality of caps until they are dispensed to the feed chute 32 and sorter 34, for example. In at least one embodiment, the hopper can comprise a body portion and a cap-dispensing portion. In such an embodiment, the body portion can comprise a bottom wall and side walls positioned around the outer perimeter of the bottom wall wherein the bottom and side walls can be configured to direct the plurality of caps to the cap-dispensing portion of the hopper to thereby aid in feeding the caps to the feed chute 32. In various embodiments, the body portion can be vibrated to further assist in feeding the plurality of caps to the cap-dispensing portion of the hopper. In at least one embodiment, the cap-dispensing portion of the hopper can comprise any suitably shaped opening therein through which the caps can pass as they are fed to the sorter. In such an embodiment, the cap-dispensing portion can further comprise a gate member positioned proximate to, and configured to slidably engage with, the opening. In various embodiments, the gate member can be configured to modify the size and/or shape of the opening in the cap-dispensing portion to accommodate the size and/or geometry of the caps being run through the automated processing line 10. In at least one embodiment, the feed rate of the hopper can be varied by modifying the size and/or shape of the opening through the use of the gate. In other various embodiments, the cap-dispensing portion of the hopper can be configured to deliver the caps at any suitable angle with respect to the feed chute 32. In such an embodiment, the angle of cap delivery can be related to the size, weight, and/or geometry of the caps being run through the automated processing line 10, for example.

Figure 2:
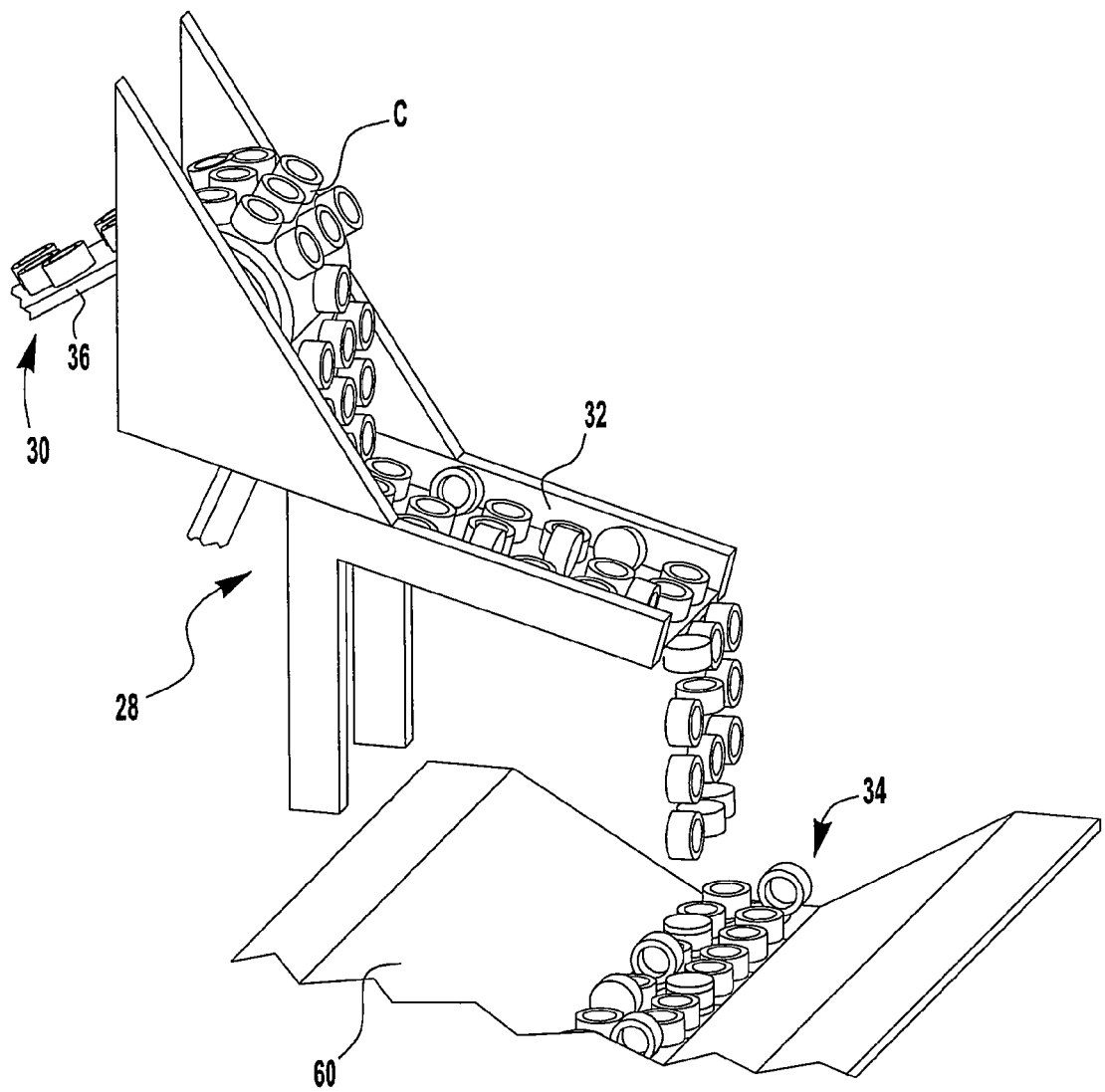
FIG. 2 is a perspective view of an elevator, a feed chute, and a sorter configured for use with a method for cap sorting and/or orienting in accordance with one non-limiting embodiment of the present invention.
Figure 3:
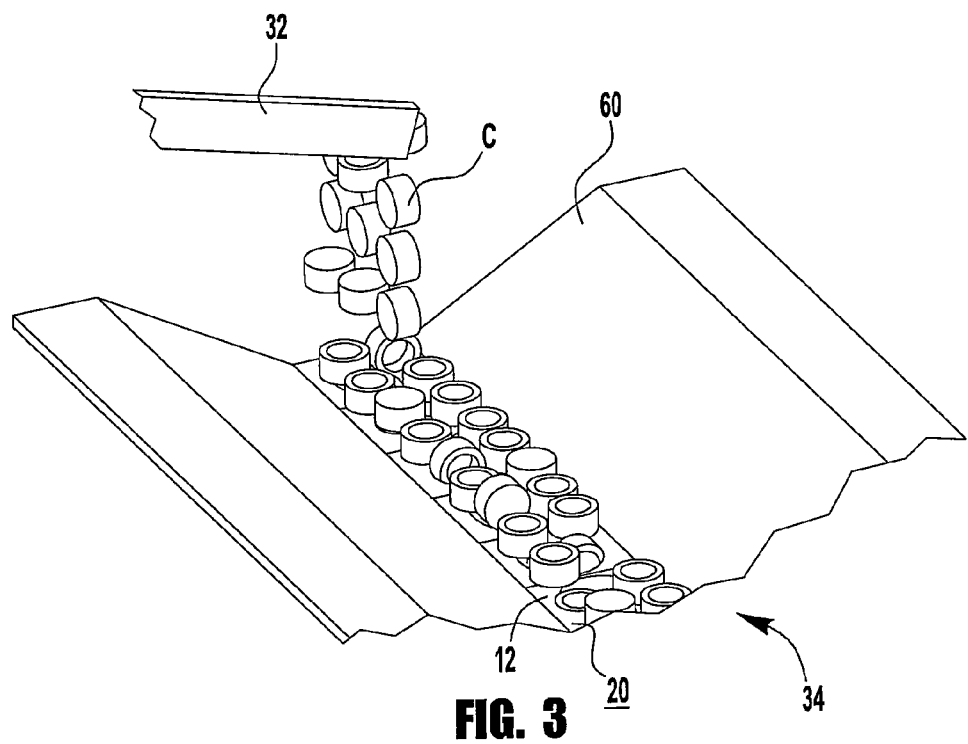
FIG. 3 is a partial perspective view of the feed chute, sorter, and side guards of FIG. 2.
Figure 4:
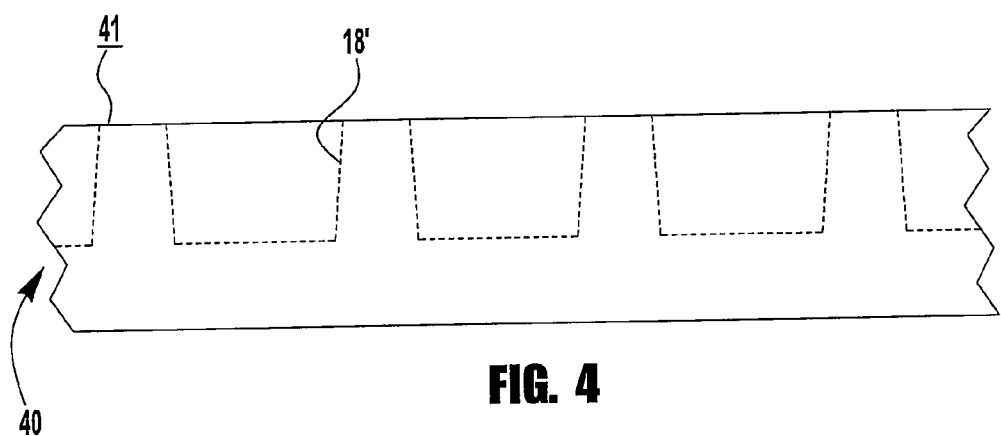
FIG. 4 is a side view of a plurality of cavities defined in a sort conveyor of a sorter in accordance with one non-limiting embodiment of the present invention.

In various embodiments, referring to FIGS. 2-5, the plurality of caps can be dispensed from the feed chute 32 and provided to a belt portion 40 of the sort conveyer 14 and/or to the top surfaces 20 of at least some of the plurality pucks 12 attached to the belt portion 40. In at least one embodiment, the belt portion 40 can include cavities 18' defined therein without the use of pucks 12 (FIG. 4). In other embodiments, the pucks 12 attached to the belt portion can include cavities 18 (FIG. 7), for example. Cavities 18 and 18' may be referred to interchangeably herein. In various embodiments, the feed chute 32 can dispense more caps than available cavities to efficiently fill at least a portion of the cavities 18 with a first group of caps 16. Stated another way, the plurality of caps can be overfed onto the pucks 12 and/or belt portion 40 to thereby increase the probability that at least most of the cavities can receive a cap. In other various embodiments, a number of caps equal to or less than the number of cavities can be fed onto the pucks and/or belt portion 40, for example. In various embodiments, the excess caps 22 not received in the cavities 18 can remain in contact with the top surfaces 20 of the portion of the plurality of pucks 12 and/or a surface 41 of the belt portion 40 until they can be removed by a cap-removal device, as discussed below. In at least one embodiment, the caps can be fed into the sorter 34 at a rate of 250 to 700 caps per minute, for example. Of course, depending on the size, weight, and/or geometry of the caps, other cap feed rates can also be appropriate and are within the scope of the present invention.

As outlined above, in various embodiments, the sorter 34 of the automated processing line 10 can comprise a sort conveyor 14 configured to receive the plurality of pucks 12, and/or other suitable cap-carrying devices. In at least one embodiment, referring to FIGS. 5-7 and 10-12, the plurality of pucks 12 can be arranged in a linear fashion and/or in a row and can be positioned adjacent to each other on the belt portion 40 of the sort conveyor 14. In other various embodiments, the plurality of pucks can be provided to the sort conveyor in a duel row fashion (not illustrated), for example, to increase the throughput of the automated processing line 10. In either configuration, the pucks 12 can each comprise a body 42 and a puck insert 44 having top surface 20, where the top surface 20 can comprise a rectangular or square shape, for example, such that the top surface 20 can include two side walls and two end walls.

In various embodiments, a puck insert 44 can be formed integral with and/or can be attached to the body 42. In at least one embodiment, the puck insert 44 can include the top surface 20 and the cavity 18 configured to receive a single cap defined in the top surface. In at least such an embodiment, a bottom surface 43 of the body 42 can be configured to be attached to the surface 41 of the belt portion 40 of the sort conveyor 14. In various embodiments, the pucks 12 can be positioned on the surface 41 such that the side walls and/or end walls of a first puck can be positioned adjacent to the side walls and/or end walls of a second puck, for example, to thereby form a planer, or substantially planer, surface across the top surfaces 20 of the plurality of pucks 12. In such an embodiment, the side-by-side placement of the pucks 12 can prevent, or at least inhibit, the plurality of caps from being settled and/or from becoming trapped in between the plurality of pucks 12.

Further to the above, in various embodiments, the surface 41 of the belt portion 40 and a bottom surface 43 of the body 42 can each comprise Velcro™ and/or an adhesive, for example, to engage the bottom surface 43 with the surface 41 of the belt portion 40. In other various embodiments, magnetic forces can be used to retain the pucks 12 and/or bottom surface 43 to the surface 41. In such an embodiment, the surface 41 can include a magnet and the bottom surface 43 can include a magnetic material, for example. In further various embodiments, the bodies 42 of the pucks 12 can be formed with and/or extend from the surface 41 of the belt portion 40. In at least one embodiment, the pucks 12 can be clamped and/or otherwise mechanically engaged with the surface 41 of the belt portion 40. In any event, the attachment of the pucks 12 to the surface 41 of the belt portion 40 can allow the pucks 12 to remain in contact with the belt portion 40 during a full rotation of the sort conveyor 14, including when the pucks 12 are hanging from the belt portion 40 as the pucks 12 are cycled about the sort conveyor 14.

Figure 13:
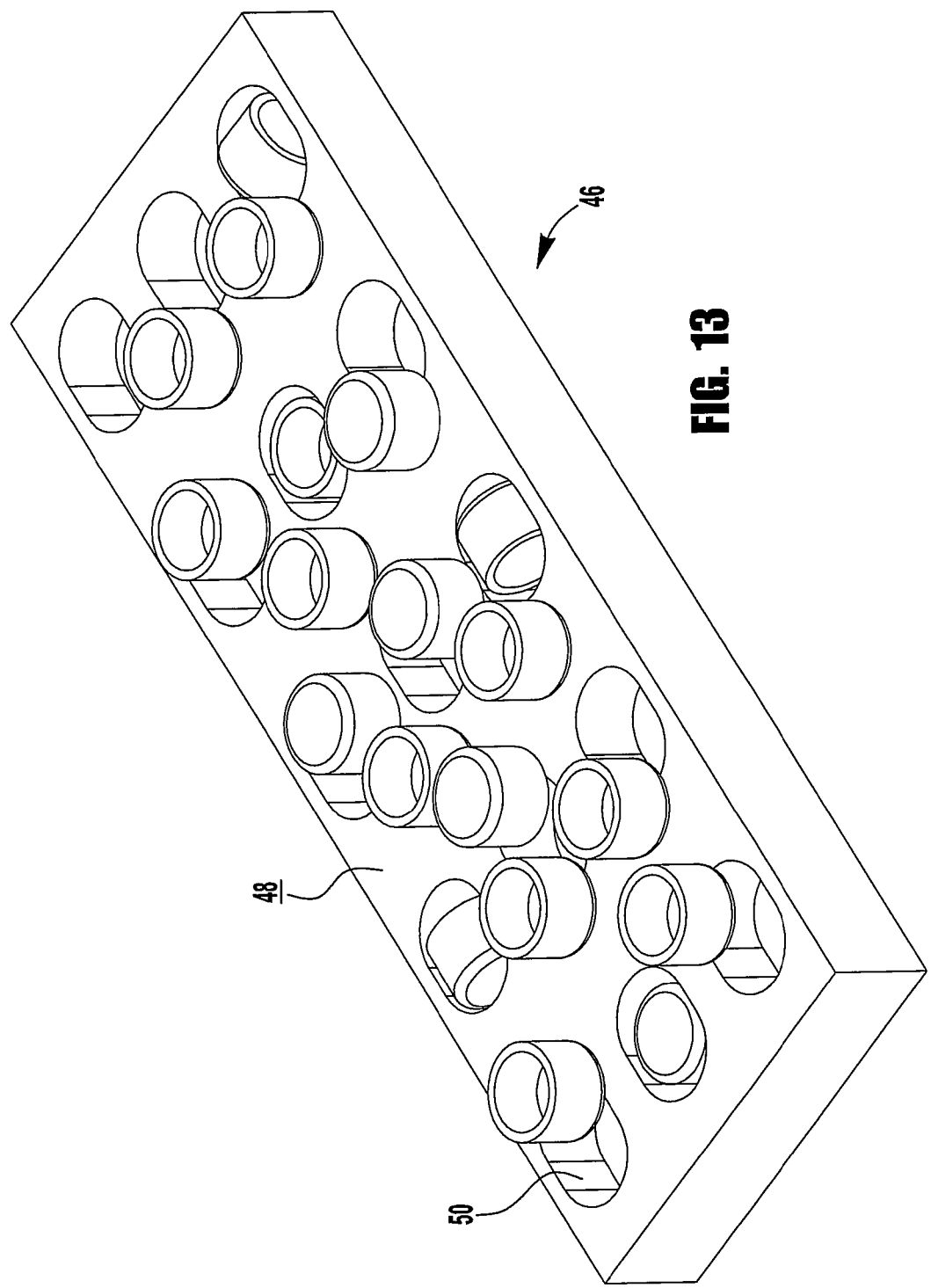
FIG. 13 is a perspective view of a tray including a plurality of cavities defined therein configured for use with a method of sorting and/or orienting caps in accordance with one non-limiting embodiment of the present invention.
Figure 14:
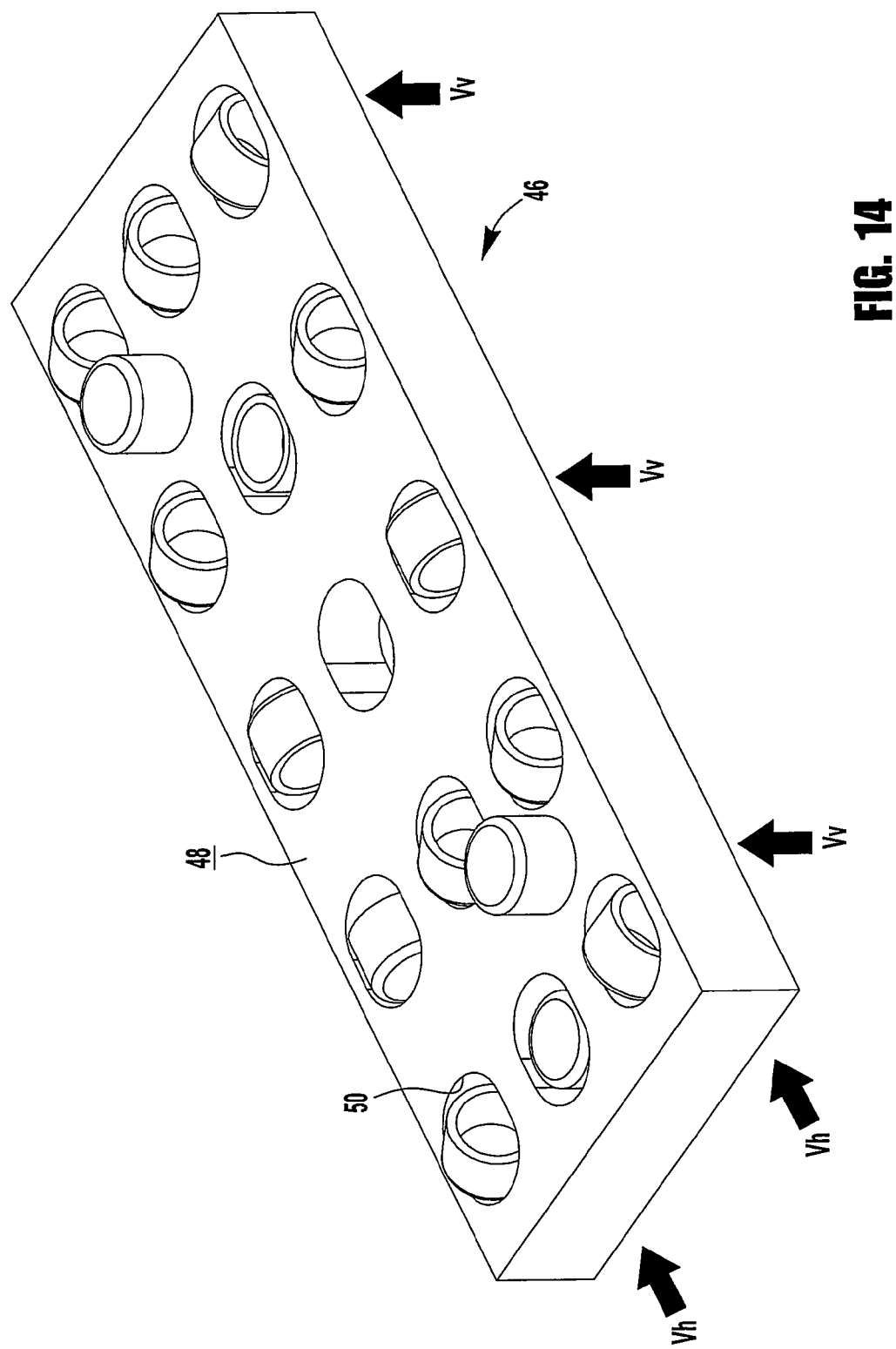
FIG. 14 is a perspective view of the tray of FIG. 13 illustrating caps positioned within at least some of the cavities and where horizontal and/or vertical vibrational energy is being applied to the tray.
Figure 15:
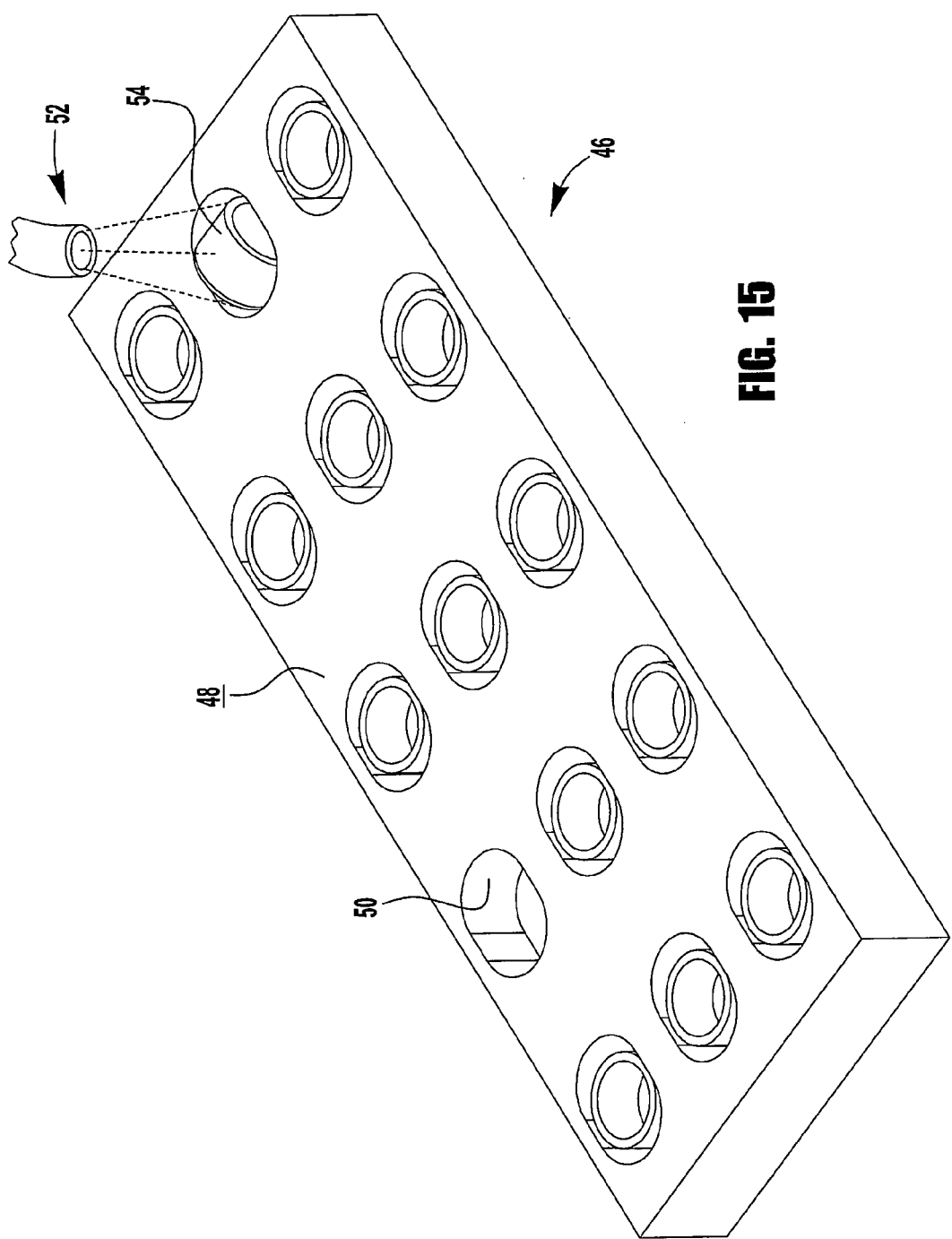
FIG. 15 is a perspective view of the tray of FIG. 14 illustrating the caps oriented to a local minimum state of potential energy and/or properly oriented position in at least some of the cavities of the tray.
Figure 16A:
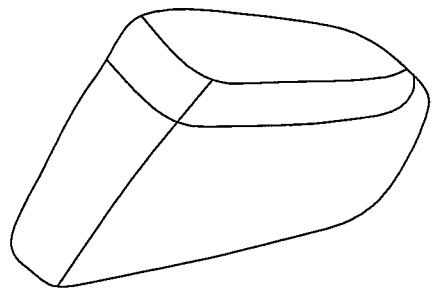
FIGS. 16A-F illustrate examples of various types of caps that can be used with the method of cap sorting and/or orienting in accordance with one non-limiting embodiment of the present invention.
Figure 16B:
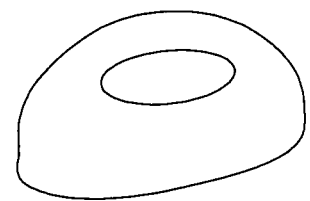
Figure 16C:
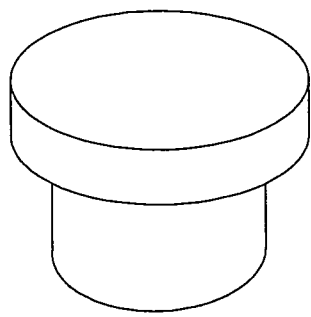
Figure 16D:
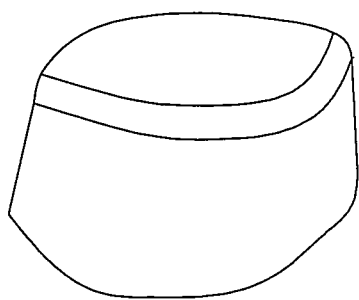
Figure 16E:
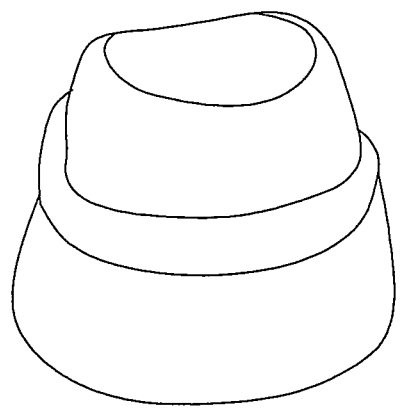
Figure 16F:
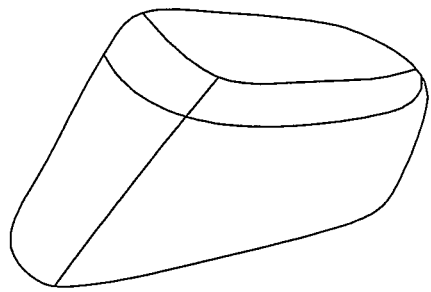
Figure 18:
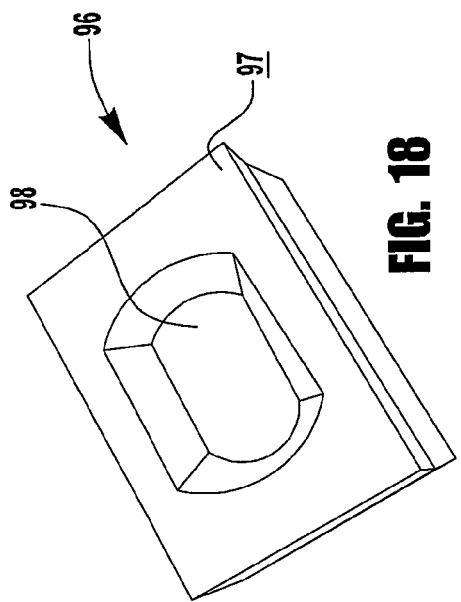
FIG. 18 is a perspective view of the mold created from the computerized model of FIG. 17.
Figure 20:
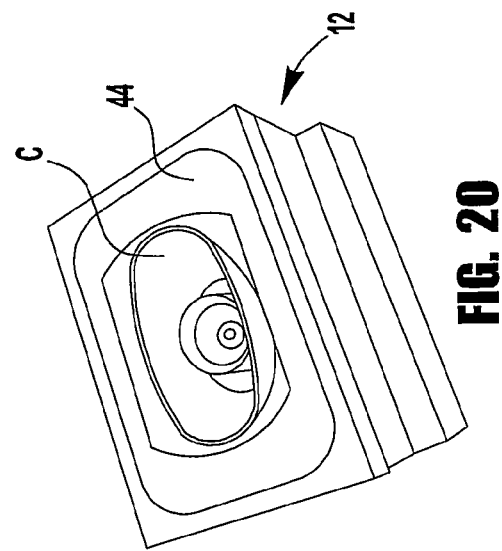
FIG. 20 is a perspective view of the puck insert of FIG. 19 attached to a puck carrier.
Figure 17:
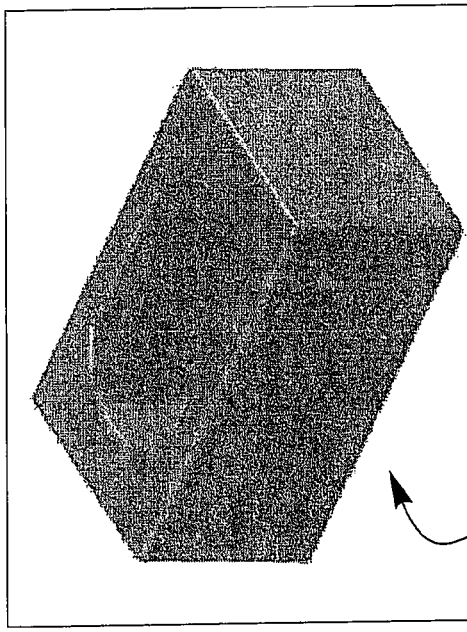
FIG. 17 illustrates a computerized model of a mold configured to create a puck insert in accordance with one non-limiting embodiment of the present invention.
Figure 19:
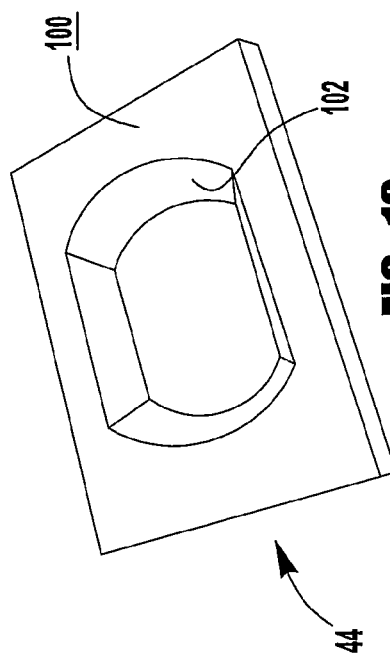
FIG. 19 is a perspective view of a puck insert created using the mold of FIG. 18.

In other various embodiments, referring to FIGS. 13-15, a tray can be configured to receive the plurality of caps. In at least one embodiment, the tray 46 can include a surface 48 having a plurality of cavities 50 defined therein. In such an embodiment, the cavities 50 can be similar to the cavities 18 defined in the pucks 12, described above. In various embodiments, the tray 46 can include any suitable number of rows and columns, for example, to achieve any suitable cap throughput. In at least one embodiment, the plurality of caps can be provided to the surface 48 and/or at least some of the cavities 50 of the tray 46 to allow at least some of the caps to settle within the cavities 50 of the tray 46. In various embodiments, the tray 50 can be attached to the belt portion 40 of the sort conveyor 14, using the attachment methods described above, and/or can be used independent of the sort conveyor 14. In at least one embodiment, a robotic arm (not illustrated) can be used to pick and place caps in the tray to thereby fill an entire row of the tray 46 and then transport the entire row of oriented caps to a capping machine, for example. Additionally, in such an embodiment, a vacuum system 52 can be used to remove any excess and/or improperly oriented caps 54 from the tray 46 (FIG. 15).

In various embodiments, the sort conveyor 14 can be configured to carry the plurality caps downstream of the feed chute 32 through the sorter 34. In at least one embodiment, the sort conveyor 14 can include a first roller positioned at a first end of the belt portion 41 and a second roller (not illustrated) positioned at a second end of the belt portion. In such an embodiment, the first and second rollers can each include a cylindrical body having an outer surface. In various embodiments, the outer surface can be configured to frictionally engage the belt portion 40 to thereby motivate the belt portion 40 around the first and second rollers. In at least one embodiment, an actuator (not illustrated) can be configured to operably engage at least one of the first and second rollers to cause the rollers to rotate about their longitudinal axis and thereby motivate the belt portion 40 about the sort conveyor 14. In such an embodiment, the sort conveyor 14 can be motivated at any suitable rate, but the rate can be directly related to the size, weight, and/or geometry of the caps being run through the automated processing line 10, for example. In various embodiments, the sort conveyor 14 can be configured to be vibrated, for example, to cause at least some of the plurality of caps to settle into at least some of the cavities 18, as described in further detail below. In at least one embodiment, the sort conveyor 14 can comprise any suitable conveyor configuration, such as a linear conveyor, a rotary conveyor, or a centrifugal conveyor, for example. In other various embodiments, the conveyor can include a curvilinear and/or arcuate shape, for example.

Further to the above, in various embodiments, referring to FIGS. 2-3, a side guard 60 can be positioned proximate to each side of the sort conveyor 14 to prevent the plurality of caps from spilling over the belt portion 40 and/or the plurality of pucks 12 and onto the area surrounding the sort conveyor 14 when the caps are fed to the sorter 34. In at least one embodiment, the side guards 60 can also prevent the excess caps 22 from sliding off of the sort conveyor 14 until the proper time for the excess cap removal. In various embodiments, the side guards 60 can be angled in an upward direction relative to the surface 41 of the belt portion 40 such that if the caps bounce or slide from the sort conveyor 14 as they are dispensed from the feed chute 32 and/or the when the caps are sorted, the caps can contact the side guards 60 and fall back onto the belt portion 40 and/or plurality of pucks 12, for example. In other various embodiments, the side guards 60 can be positioned perpendicular to, or substantially perpendicular to, the surface 41 of the belt portion 40. In any configuration, the side guards 60 can be comprised of any suitable material, such as fiberglass or plastic, for example.

As described above, in various embodiments, the pucks 12 can each include a cavity 18 defined in their top surface 20 where the cavity 18 can be configured to receive a single cap. In other various embodiments, the cavities 18' can be formed integral with the belt portion 40 of the sort conveyor 14 without the use of the pucks 12, as discussed above. In either event, the cavities 18 can each be configured to receive and/or orient a single cap. In further various embodiments, the cavities 18 can be sized large enough to allow a single cap to be oriented and/or rotated within the cavities 18, but can be sized small enough to prevent more than one cap from engaging a single cavity. Stated another way, the cavities 18 can each be sized to eliminate, or at least inhibit, two caps from being nested and/or locked within any particular cavity. In various embodiments, the cavities 18 can be configured to retain a cap situated therein when moving past the cap-removal device 62, as discussed below. In at least one embodiment, a portion of the cap can extend from the cavity while situated therein, or, in other various embodiments, about a third or a half of the cap can extend from the cavity, for example.

In various embodiments, as the sort conveyor 14 motivates the pucks 12 further downstream in the sorter 34, the pucks 12 can be conveyed past a cap removal device configured to remove the excess caps 22 from the top surfaces 20 of at least a portion of the pucks 12 and/or from at least a portion of the surface 41 of the belt portion 40. In at least one embodiment, the use of a cap removal device can increase the efficiency of the automated capping line 10 by 20 to 40 percent, for example. In various embodiments, referring to FIG. 5, the cap removal device 62 can include a nozzle 64 configured to emit a fluid stream proximate to the top surfaces 20 of at least some of the pucks 12 to thereby remove the excess caps 22 therefrom, while not interfering with the first group of caps 16 within the cavities 18. In various embodiments, the fluid stream can be comprised of air and/or other suitable fluid, for example. In at least one embodiment, the fluid stream can be configured to be emitted perpendicular and/or transverse to the direction of movement of the sort conveyor 14.

Figure 6:
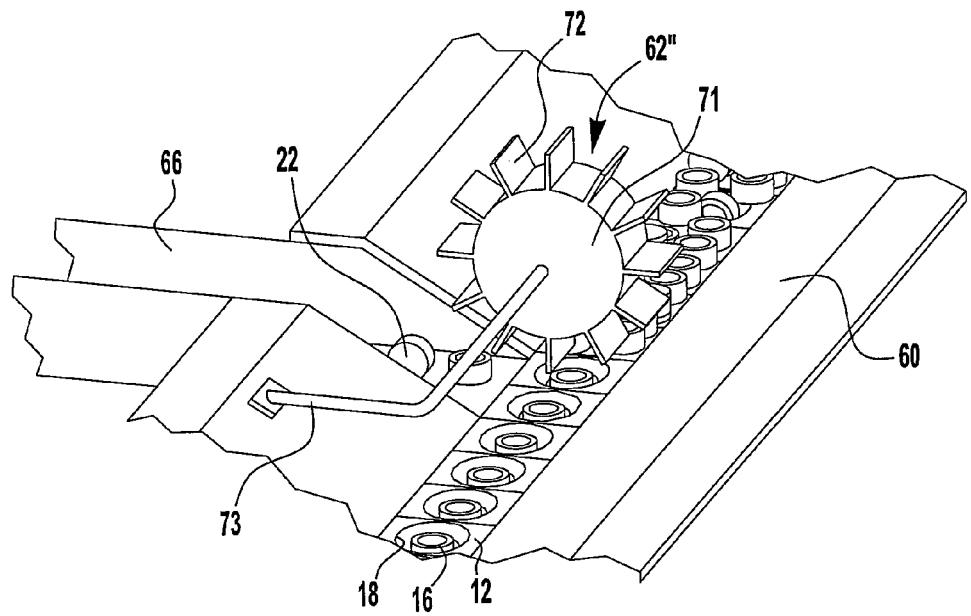
FIG. 6 is a perspective view of a sorter comprising a cap removal device including a rotary flapper in accordance with one non-limiting embodiment of the present invention.

In various embodiments, more than one fluid stream can be emitted from the nozzle 64 such that a first fluid stream can be configured to be emitted at a first distance above the top surfaces 20 of at least some of the pucks 12 and a second fluid stream can be configured to be emitted at a second distance above the top surface of at least some of the pucks. In at least one embodiment, the first distance can be less than the second distance to provide for efficient removal of the excess caps 22. In such an embodiment, the first fluid stream can be configured to be emitted at a distance of about 0-5 mm above the top surfaces 20 of at least some of the pucks 12, while the second fluid steam can be configured to be emitted about 0-10 mm above the top surfaces 20 of at least some of the pucks 12, for example. In other embodiments, the first fluid steam can be configured to be emitted at a distance of about 0-5 mm above a top edge of the cavities 18, while the second fluid stream can be configured to be emitted about 0-10 mm above the top edge of the cavities 18, for example. In further various embodiments, any other suitable distances can be used. In various embodiments, the first and second fluid streams can be emitted from one or more nozzles and/or more than two fluid streams can be emitted from one nozzle, for example. In such an embodiment, the first fluid stream can be used to separate the excess caps 22 from the pucks 12 and the second fluid stream can be used to force the excess caps 22 away from the pucks 12 and into an aperture 66 in the side guards 60 (FIG. 6). In various embodiments, the fluid flow emitted by the nozzle can include a pressure of about 10-25 p.s.i., for example. In at least one embodiment, other suitable fluid pressures can be used based on factors, such as size, weight, and/or geometry of the caps and/or the configuration of the nozzle, for example.

Further to the above, in various embodiments, the nozzle 64 can include any suitable configuration and can be mounted in any suitable fashion such that it can emit a fluid stream configured to contact and remove the excess caps 22 from the sort conveyor 14. In at least one embodiment, the nozzle 64 can include a flat nozzle comprising a plurality of apertures defined in an end most distal from a fluid supply source (not illustrated). In such an embodiment, the fluid supply source can comprise a pump and/or a compressor and can be in fluid communication with the nozzle via a conduit 65, for example. In other various embodiments, any other suitable nozzle can be connected to the fluid supply source. In at least one embodiment, the nozzle can be mounted on an end of a semi-rigid fluid supply line, for example, or, in other various embodiments, the nozzle can be slidably attached to a nozzle mount (not illustrated) situated proximate to the sort conveyor 14. In such an embodiment, the nozzle's position with respect to the sort conveyor 14 can be replicated during each run of a type particular type of cap to achieve a similar cap sorting efficiency, for example. In various embodiments, the nozzle mount can include indicia configured to aid an operator in adjusting the nozzle 64 for a particular cap size, weight, and/or geometry such that a similar cap removal efficiency can be achieved during each run of similar caps. In further various embodiments, the nozzle 64 can be adjusted for a particular cap size, weight, and/or geometry using an automated adjustment device, for example.

In various embodiments, the size, weight, and/or geometry of the caps can be some of the factors to be considered when positioning the nozzle 64 relative to the sort conveyor 14. In various embodiments, the nozzle 64 can be moved proximal to, or distal from, the sort conveyor 14 and/or the plurality of pucks 12 to adjust the force by which the fluid stream can contact the excess caps 22. In at least one embodiment, larger and/or heavier caps may require higher fluid stream pressures and/or closer nozzle positions, while smaller and/or lighter caps may require lower fluid stream pressures and/or more distal nozzle positions, for example. In such an embodiment, if the flow of the fluid stream is too strong, the fluid steam can improperly remove the first group of caps 16 from the cavities 18. Conversely, if the flow of the fluid stream is too weak, the fluid stream may not properly remove the excess caps 22 from the top surfaces 20 of the pucks 12 thereby reducing the efficiency of the automated processing line 10. As discussed above, in various embodiments, the cavities 18 can be configured to retain the first group of caps 16, while allowing the fluid stream to remove the excess caps 22.

Figure 7:
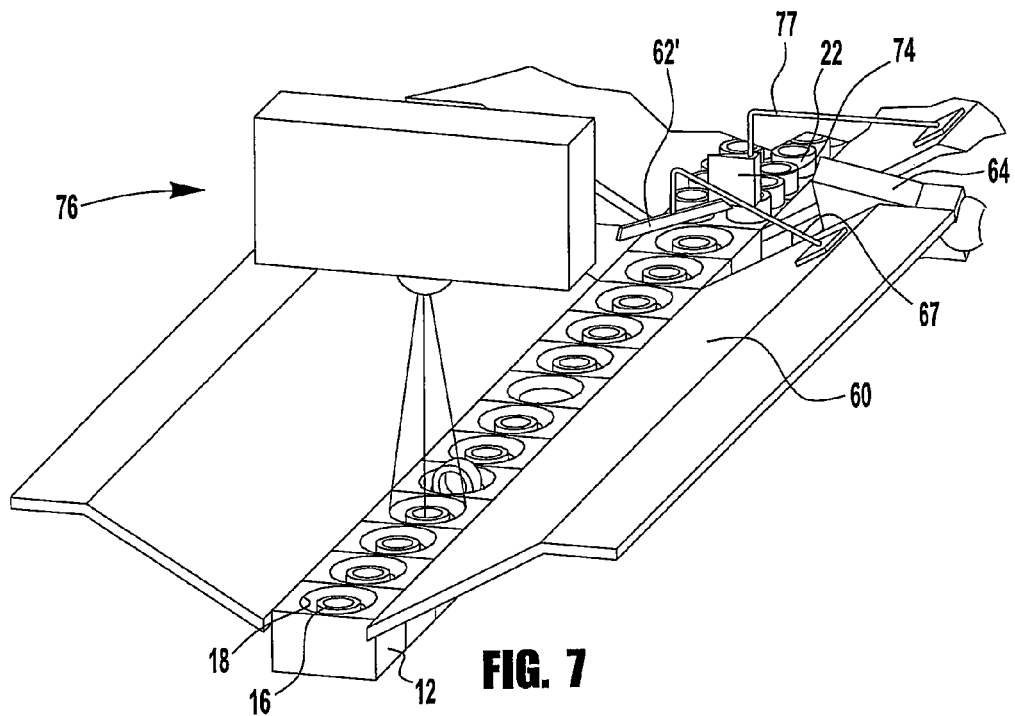
FIG. 7 is a perspective view of a sorter comprising a cap removal device including a cap wiper, and a vision system in accordance with one non-limiting embodiment of the present invention.

In further various embodiments, referring to FIG. 7, a cap removal device 62' can include a cap wiper, either in addition to or in lieu of the nozzle described above. In at least one embodiment, the cap wiper can include an elongate member configured to engage the excess caps 22 and push them into the aperture 66. In such an embodiment, the elongate member can be configured to be pivoted and/or moved over the top surfaces 20 of the pucks 12 and/or the surface 41 of the belt portion 40 such that it can contact the excess caps 22 and force them into the aperture 66. In various embodiments, the motion of the elongate member can remove the excess caps 22 from the top surfaces 20 of the pucks 12 and/or belt portion 41, while not interfering with the first group of caps 16 situated within the cavities. In such an embodiment, the cap wiper 62' can be mounted on a bracket 67 positioned over the sort conveyor 14, for example.

In other various embodiments, referring to FIG. 6, a cap removal device 62" can include a rotary flapper, either in addition to or in lieu of the cap removal devices described above. In at least one embodiment, the rotary flapper can be mounted on a bracket 73 and can include a hub 71 having a plurality of projections 72 extending outwardly from the outer perimeter of the hub. In such an embodiment, the projections 72 can be configured to engage the excess caps 22 and force and/or push them into the aperture 66 in the side guard 60 when the hub 71 is rotated about the bracket 73 in a suitable direction. In various embodiments, the hub 71 can include and/or can be operably engaged with an actuator configured to rotate the hub 71, for example. In at least one embodiment, the rotary flapper can be positioned above the sort conveyor 14 such that it can contact the excess caps 22, while not interfering with the first group of caps 16 positioned within the cavities 18.

In various embodiments, referring to FIG. 7, a cap director 74 can be mounted on a bracket 77 and can extend over a portion of the sort conveyor 14 opposite from the aperture 66. In at least one embodiment, the cap director 74 can be configured to aid in the removal of the excess caps 22. In such an embodiment, the cap director 74 can include an angled surface configured to engage the excess caps 22, as the caps approach the cap director, and direct them towards the aperture 66, for example. In various embodiments, the nozzle, cap wiper, and/or rotary flapper can be used in conjunction with the cap director 74 to improve the efficiency of the excess cap removal.

Figure 5:
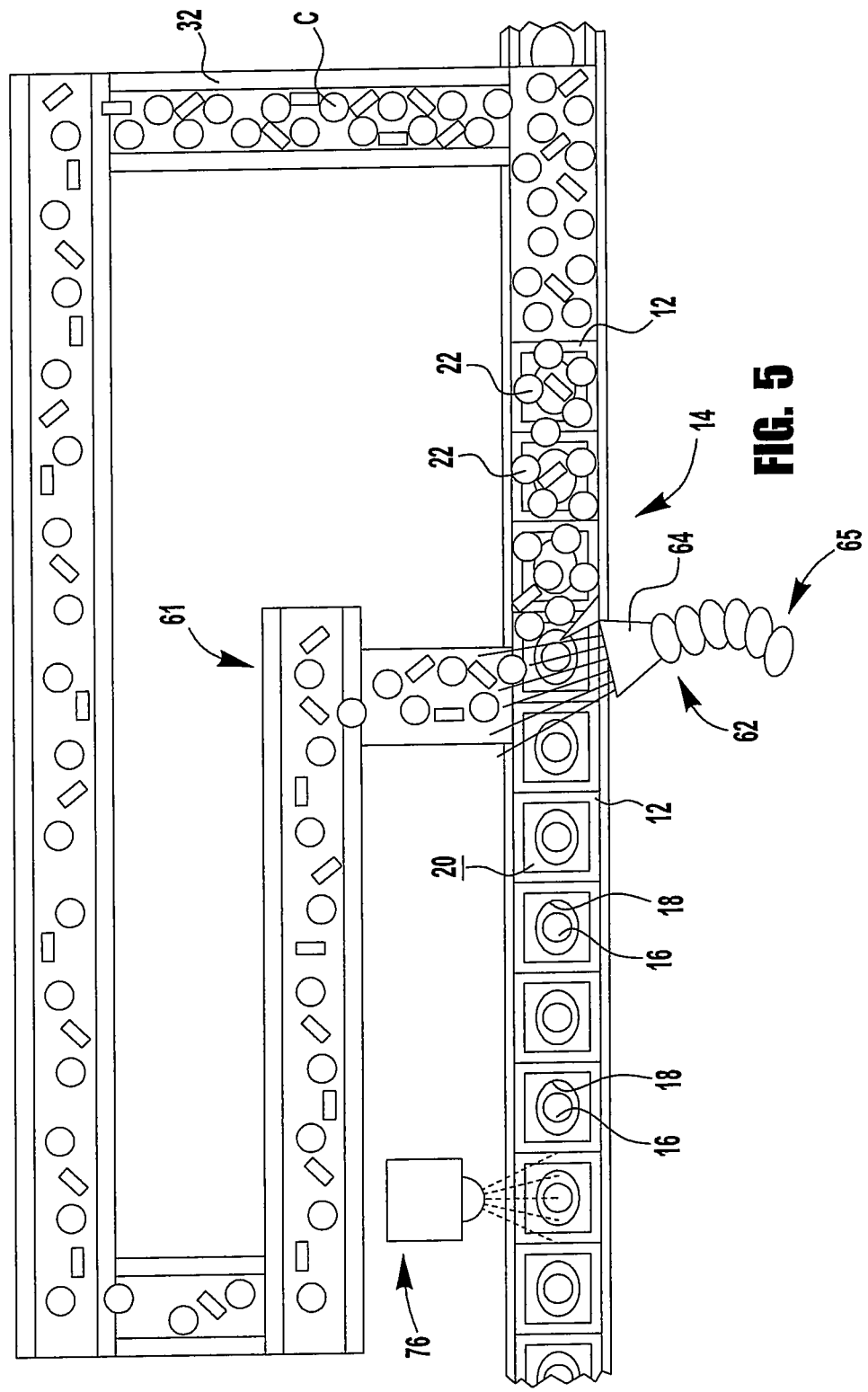
FIG. 5 is an overhead view of the components configured for use with a method of cap sorting and/or orienting, including a cap removal device, in accordance with one non-limiting embodiment of the present invention.

In various embodiments, referring to FIG. 5, the excess caps 22 can be forced through the aperture 66 in the side guard 60 and can engage a cap return conveyor 61. In at least one embodiment, the cap return conveyor 61 can convey the excess caps 22 back to the elevator 30 of the feeder 28 such that the excess caps 22 can again be reintroduced into the feed chute 32 and again fed into the sorter 34. In other various embodiments, the excess caps 22 can be conveyed to a second hopper (not illustrated) and can be reintroduced to the elevator 30, as needed, or can remain within the second hopper if a cap change-over is about to occur in the automated processing line. In other various embodiments, the excess caps 22 can be reintroduced onto the sort conveyor 14 at a point downstream of the cap removal device 62. In at least one embodiment, the return conveyor can directly convey the excess caps 22 back onto the sort conveyor 14 and/or the return conveyor can work in conjunction with a second elevator and a second feed chute to convey to excess caps back onto the sort conveyor, for example. In such an embodiment, the sort conveyor can again be vibrated to cause the caps to settle into the cavities 18, as described herein. In at least one embodiment, the reintroduction of the excess caps 22 to the sort conveyor 14 can increase the efficiency of the system by providing the chance that any empty cavities will be filled by a reintroduced cap. In various embodiments, a second cap removal device (not illustrated) can then be used to remove any excess caps from the sort conveyor 14, for example. In at least one embodiment, the second cap removal device can be similar to the cap removal devices described above.

Figure 12:
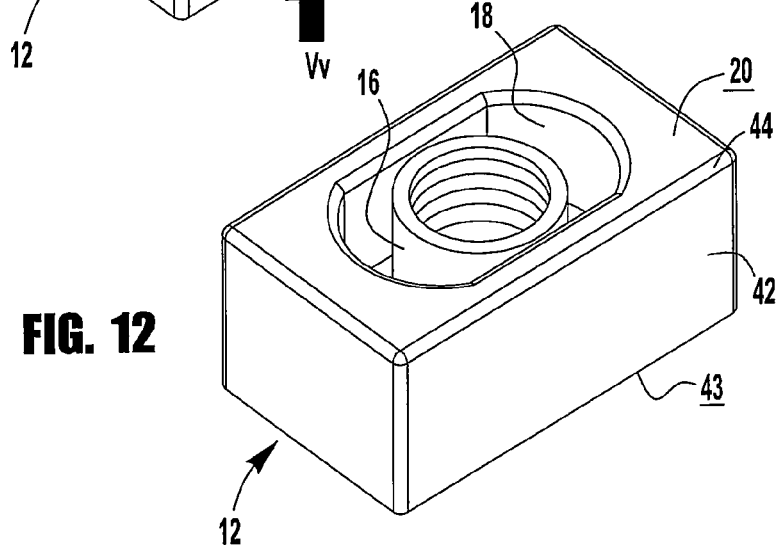
FIG. 12 is a perspective view of the single puck of FIG. 10 illustrating the cap oriented in its local minimum state of potential energy and/or properly oriented position.

In various embodiments, once the first group of caps 16 has been situated into at least some of the cavities 18, as described above, at least some of the caps can be oriented within the cavities 18 by introducing vibrational energy to at least a portion of the pucks 12 and/or at least a portion of the sort conveyor 14. In at least one embodiment, referring to FIGS. 10-12, the vibrational energy can include the application of vertical vibration ($V_h$) and/or horizontal vibration ($V_h$), for example. In such an embodiment, the vibrational energy can cause the caps within at least some of the cavities 18 to orient into a position of lowest energy, or, stated another way, to a position where the caps can each achieve a local minimum state of potential energy (FIG. 12). In other various embodiments, the caps can each achieve a minimum state of potential energy within the cavities 18, for example. In still other various embodiments, the caps can be oriented to any desired position. In at least one embodiment, the sort conveyor 14 and/or the pucks 12 attached to the conveyor can be configured to slide and/or move in a leftward and rightward direction and/or an upward and downward direction when operably engaged with an actuator configured to provide the vibrational energy. In such an embodiment, the actuator can be configured to vibrate the sort conveyor and/or the pucks in a horizontal and/or vertical direction, for example. In at least one embodiment, more than one actuator can be provided, such that a first actuator can cause horizontal vibration and/or movement of the sort conveyor and/or the pucks and a second actuator can cause vertical vibration and/or movement of the sort conveyor and/or the pucks, for example.

In various embodiments, the amount of vibrational energy need to properly orient the caps within the cavities can be proportional to the size, weight, and/or geometry of the caps being run through the automated processing line 10. In such an embodiment, to achieve proper orientation of the caps within the cavities, smaller, and/or lighter caps can require a lesser input of vibrational energy, while larger and/or heavier caps can require a greater input of vibrational energy, for example. In various embodiments, the vibration applied to the sort conveyor and/or pucks by the actuator can have an amplitude between about 1.5 and 4 mm, i.e., about 3-8 mm displacement, for example, and can have a frequency adjustment between about 8 and 15 Hertz, for example. In other various embodiments, any suitable vibration amplitude and/or frequency can be used for a particular cap size, weight, and/or geometry.

In various embodiments, the vibrational energy can be applied to the sort conveyor through the use of an eccentric and/or cam (not illustrated) mounted on and substantially perpendicular to a drive shaft of the actuator. In at least one embodiment, the eccentric can include a projection extending perpendicular to the plane of the eccentric and proximate to the outer perimeter of the eccentric wherein the projection can be attached to a first end of an elongate shaft. In such an embodiment, a second end of the elongate shaft can be operably engaged with a portion of the sort conveyor 14 and/or the pucks 12. In various embodiments, the elongate shaft can extend in a direction substantially parallel to the plane of the eccentric and substantially perpendicular to the projection and drive shaft, for example, such that as the eccentric is rotated by the drive shaft, the elongate shaft can be displaced in a forward and rearward direction and/or an upwards and downwards direction, i.e. reciprocation. Stated another way, the rotational motion of the drive shaft can be converted into linear motion and/or reciprocation of the elongate shaft. In various embodiments, the linear motion of the elongate shaft can be used to apply the vibration to the sort conveyor and/or pucks, for example. In at least one embodiment, the size of the eccentric and/or the attachment point of the projection to the eccentric can be adjusted to vary the length of displacement of the elongate shaft and thereby the amplitude of the vibration applied to the sort conveyor and/or the pucks. In various embodiments, the rotational speed of the drive shaft can also be adjusted to vary the frequency of the vibration, for example. In other various embodiments, any suitable mechanism configured to convert rotational motion of the drive shaft into linear motion and/or reciprocation of the elongate shaft can be used. In still other various embodiments, any suitable means for vibrating the sort conveyor and/or pucks can be used.

In various embodiments, the tray, described above, can also be configured to receive a horizontal vibration ($V_h$) and/or a vertical vibration ($V_v$) to orient the caps to a local minimum state of potential energy and/or desired position within the cavities 50. In at least one embodiment, referring to FIGS. 14 and 15, the tray 46 can be vibrated similar to the sort conveyor 14 and/or pucks 12 described above. In various embodiments, if the tray 46 is used independent of the sort conveyor 14, the caps of the tray 46 can be transferred to the capping machine using the robotic arm described above. In at least one embodiment, if the tray 46 is positioned on the sort conveyor 14, the tray 46 can function similar to the pucks 12 described herein. As outlined above, a duel-row tray can be attached to the sort conveyor 14, for example, to increase the throughput of the capping line 10. In at least one embodiment, the tray 46 can be used in conjunction with a vision system, similar to the vision system described below.

In various embodiments, the caps within the cavities can be supported in at least five degrees of freedom, i.e., three-translational and two-rotational, when in the properly oriented position. In at least one embodiment, the three translational degrees of freedom can include support from the cap moving upwards and downwards, left and right, and forward and backwards. In such an embodiment, the two rotational degrees of freedom can include support from the cap turning upwards and downwards and tilting side to side. In various embodiments, to support the caps in the properly oriented position with the five degrees of freedom can require the cap to increase in energy before the cap can be positioned in the local minimum state of potential energy and/or the properly oriented position. In such an embodiment, the increase in energy needed to orient the cap to the local minimum state of potential energy can be provided in the form of horizontal and/or vertical vibrational energy, as described above. In various embodiments, the input of the vibrational energy can cause at least some of the caps to become oriented in a local minimum state of potential energy within the cavities. In at least one embodiment, the local minimum state of potential energy of the caps can be achieved when the center of gravity of the caps is in its lowest position within the cavities, for example. In various embodiments, a top portion of the cap can be heavier than a bottom portion of the cap owing to the fact that the top portion can include a product-dispensing nozzle which can be heavier than the outer shell and aperture of the bottom portion, for example. For at least the above-referenced reasons, in various embodiments, the top portion of the cap can be oriented downwards within the cavity thereby causing the outer shell and aperture of the cap to be oriented upwards after the vibrational energy is applied to the pucks and/or sort conveyor.

In various embodiments, after at least some of the caps are oriented to the local minimum state of potential energy and/or properly oriented position within the cavities, the caps can continue downstream on the sort conveyor 14 and can be viewed by a vision system 76, such as a Cognex® vision system, for example. In at least one embodiment, referring to FIGS. 4 and 7, the vision system 76 can be positioned above a portion of the sort conveyor 14 and/or a portion of the pucks 12 such that the vision system 76 can have a direct line of sight into the passing cavities 18 and first group of caps 16 situated therein. In such an embodiment, the vision system 76 can be configured to determine whether a particular cap's orientation within a cavity is proper (nozzle top down) or improper (nozzle top sideways or up). In other various embodiments, the vision system can be configured to determine any desired cap configuration and/or if the cavity is empty. In various embodiments, the vision system 76 can include an optical lens portion configured to view the caps and a microprocessor configured to receive a signal indicative of a cap's orientation from the optical lens portion, for example. In at least one embodiment, the vision system 76 can be used in conjunction with at least one ancillary light source to illuminate the cavities 18 and aid the vision system in determining proper verses improper cap orientation.

Further to the above, in various embodiments, if the microprocessor of the vision system receives a signal indicative of a proper cap orientation, the microprocessor can transmit an output signal to a cap carrier dispenser 78 causing the dispenser to deploy a cap carrier 24 to a top surface 20 of a particular puck 12 and/or to the surface 41 surrounding a particular cavity. In other various embodiments, if the microprocessor receives a signal indicative of improper cap orientation it may not transmit the output signal to the cap carrier dispenser 78 causing the dispenser to not deploy a cap carrier 24. In at least one embodiment, the microprocessor may transmit an output signal indicating to the cap carrier dispenser 78 to not dispense the cap carrier 24, for example. As a result of the above, only the cavities having a properly oriented cap may receive a cap carrier 24 thereby eliminating cap carriers 24, without caps, from being conveyed to the capping machine 26 and creating an inefficient capping result.

Figure 8:
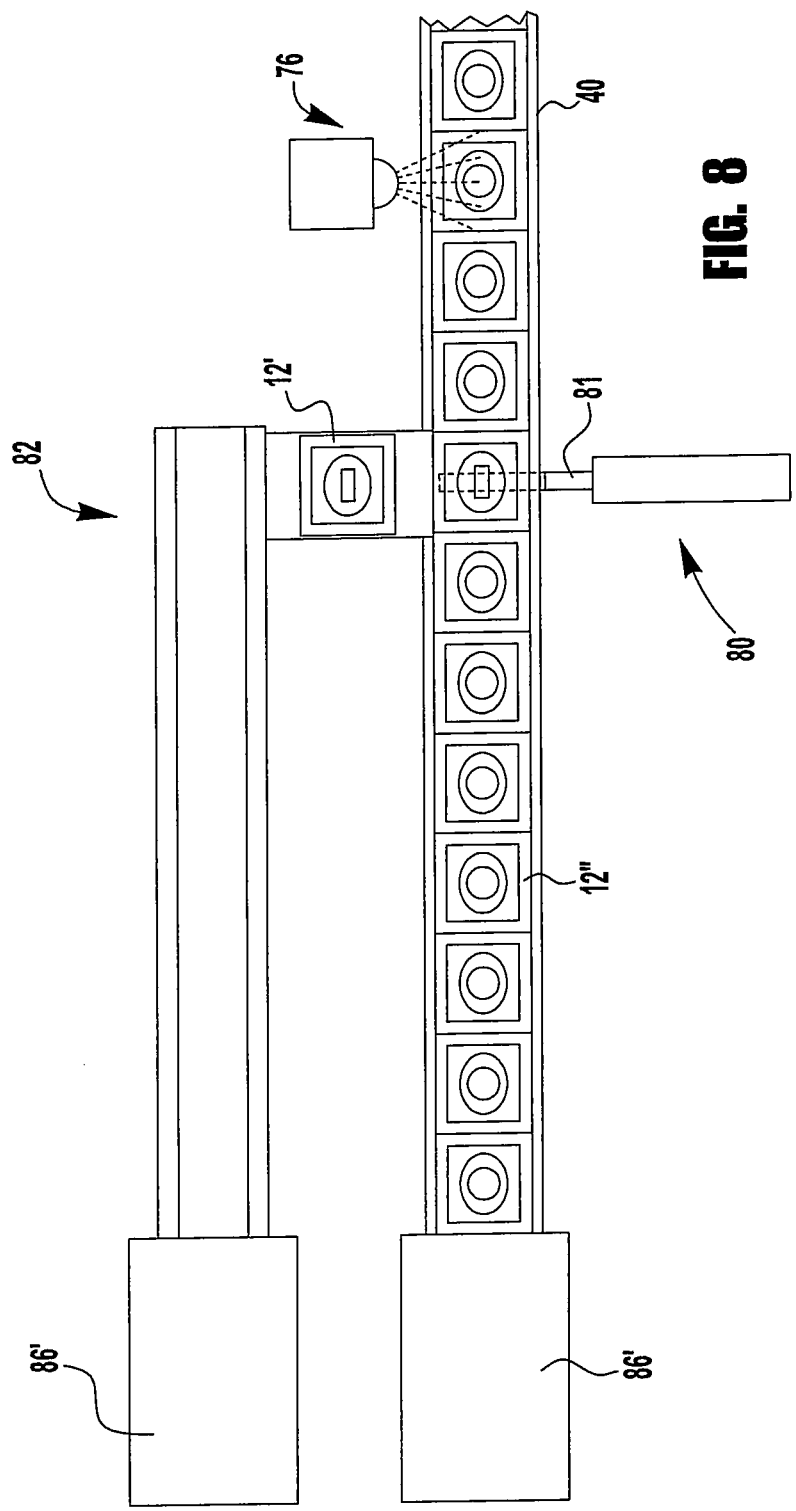
FIG. 8 is an overhead view of the components, including a bad puck lane, configured for use with a method of sorting and/or orienting caps in accordance with one non-limiting embodiment of the present invention.

In other various embodiments, referring to FIG. 8, either in addition to or in lieu of the vision system in communication with the cap carrier dispenser, as described above, the vision system can be in communication with a puck pusher 80, or other suitable device, configured to separate the pucks having improperly oriented caps, non-desired orientations, and/or empty cavities, onto a bad sort conveyor 82. In at least one embodiment, the puck pusher 80 can include an actuator including a piston 81, for example, where the piston can be configured to push any bad pucks 12' from the sort conveyor 14 and onto the bad sort conveyor 82. In such an embodiment, the puck pusher 80 can be configured to receive an output signal from the vision system indicative of a proper or an improper cap orientation within a particular cavity. In various embodiments, the puck pusher 80 can deploy the piston 81 to push the bad pucks 12' onto the bad sort conveyor 82 when it receives a signal indicative of an improper cap orientation, and not deploy the piston 81 when it receives a signal indicative of a proper cap orientation, for example. In such an embodiment, the piston 81 can be configured to deploy and retract quickly such that it only contacts a specified puck. As a result, only good pucks 12" having properly oriented cap will be conveyed past the cap carrier dispenser 78 (not illustrated in FIG. 8) to receive a cap carrier 24.

In various embodiments, as described above, the pucks can be attached to the sort conveyor by magnets, for example, where the piston 81 of the puck pusher 80 can apply a force to the bad pucks 12' sufficient to overcome the attractive force applied by the magnets. In various embodiments, the piston 81 of the puck pusher 80 can be activated electrically, hydraulically, and/or pneumatically, for example, when it receives a signal indicative of an improper cap orientation from the vision system 76. In at least one embodiment, the puck pusher 80 can eliminate the need for the cap carrier dispenser 78 to selectively dispense cap carriers 26 to only the pucks having properly oriented caps. In this embodiment, the cap carrier dispenser 78 can dispense a cap carrier 26 to each good puck 12" on the sort conveyor 14, owing to the fact that only the good sort pucks 12" travel downstream on the sort conveyor 14 to the cap carrier dispenser 78. In various embodiments, the bad sort conveyor 82 can be configured to eject and/or dump the improperly sorted cap into a hopper, using a cap transfer slide 86', similar to cap transfer slide 86 described below. In at least one embodiment, the caps in the hopper can be conveyed back to the elevator 30 to again be deployed by the feed chute 32, for example. In such an embodiment, the now empty pucks can be returned to the sort conveyor 14 to again receive caps deployed from the feed chute 32.

As described above, in various embodiments, the cap carrier dispenser 78 can be located downstream of the vision system 76 and can be configured to deploy a cap carrier 24 to a top surface 20 of each puck 12 and/or to each puck and/or cavity having a properly sorted cap. In at least one embodiment, the cap carrier dispenser 78 can include a microprocessor configured to receive the output signal transmitted by the microprocessor of the vision system, as described above. In such an embodiment, the microprocessor of the vision system 76 can interpret the signal received from the cap carrier dispenser 78 to determine whether to deploy a cap carrier 24 to a particular puck 12 and/or to the surface 41 surrounding a cavity. In various embodiments, the cap carrier dispenser 78 can include a cap carrier deploying mechanism (not illustrated) configured to place and/or drop the cap carrier 24 onto the top surface 20 of the puck 12 and/or the surface 41.

Figure 9:
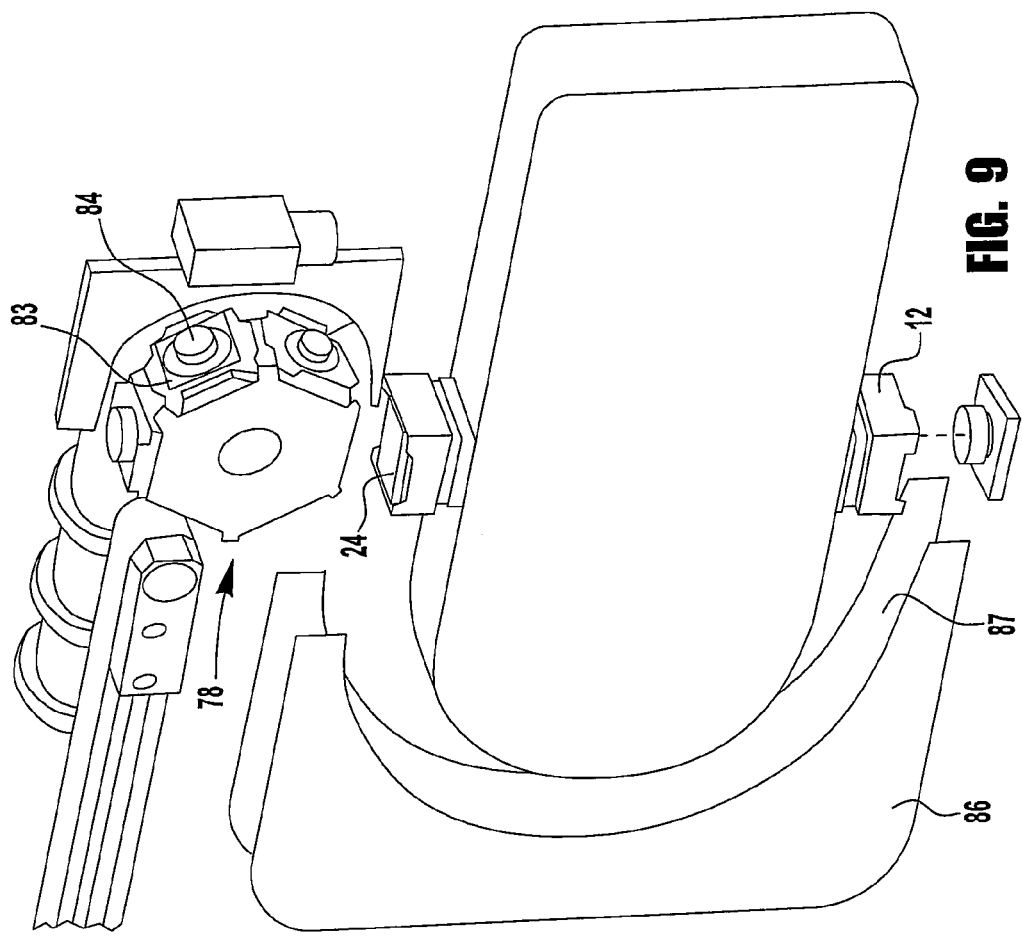
FIG. 9 is a perspective view of a cap carrier dispenser and a cap transfer slide which is configured to transfer a cap from the puck to a cap carrier in accordance with one non-limiting embodiment of the present invention.
Figure 10:
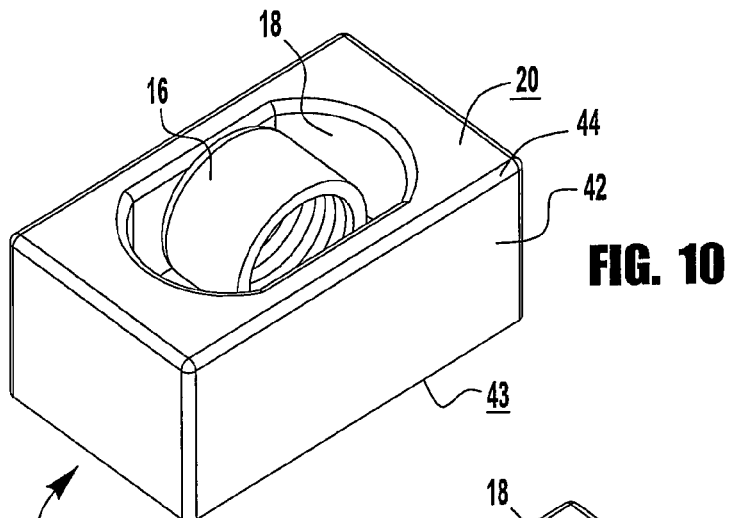
FIG. 10 is a perspective view of a single puck including a cavity having an improperly oriented cap situated therein in accordance with one non-limiting embodiment of the present invention.
Figure 11:
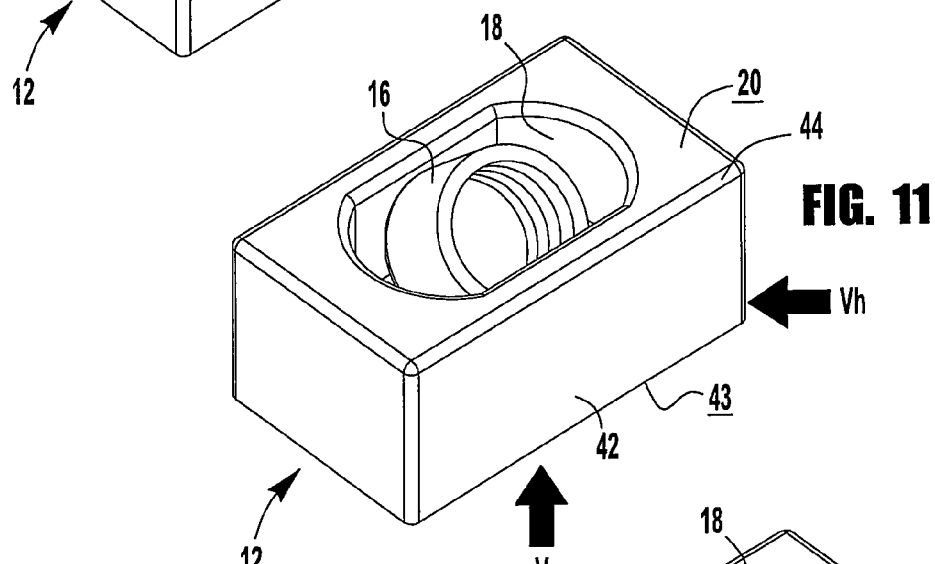
FIG. 11 is a perspective view of the single puck of FIG. 10 illustrating horizontal and/or vertical vibrational energy being applied to the puck to orient the cap within the cavity.

In various embodiments, referring to FIG. 9, the cap carrier 24 can include a body portion 83 and a cap-engaging portion 84 extending outwardly from the body portion where the cap-engaging portion 84 can be configured to engage the aperture defined by the outer shell of the cap. In at least one embodiment, the body portion 83 of the cap carrier 24 can have a similar shape as the top surface 20 of the puck 12 to allow the cap carrier 24 to easily engage the puck 12. In such an embodiment, as the cap carrier 24 engages the top surface 20 of the puck 12, the cap-engaging portion 84 can engage the aperture of the cap, for example. In various embodiments, the engagement between the cap-engaging portion 84 and the aperture can be loose-fitting such that the cap can easily be retrieved by a chuck 90 of the capping machine 26, for example. In other various embodiments, the engagement of the cap-engaging portion 84 and the aperture can include a friction-fit such that the cap can be retained to the cap-engaging portion 84 for transport to the capping machine 26.

In various embodiments, referring to FIG. 9, the pucks 12 on the sort conveyor 14, which have the cap carriers 24 engaged thereon, can continue to travel downstream in the automated capping line 10 and can engage a cap transfer slide 86 located near the first end of the sort conveyor 14 most distal from the feed chute 32. In at least one embodiment, the cap transfer slide 86 can include an arcuate track 87 configured to mimic the shape of the first end of the sort conveyor 14, for example. In such an embodiment, the puck can travel around the first end of the sort conveyor 14 while the cap carrier 24 can engage the track 87 in the cap transfer slide 86. In various embodiments, the track 87 can be configured to maintain the cap carrier 24 in contact with the puck 12 as the puck travels around the first end of the sort conveyor 14. In at least one embodiment, the puck 12 can be inverted from an upright position to an upside down position as it travels around the first end of the sort conveyor 14, for example. In such an embodiment, upon the cap carrier 24 disengaging the track 87, the puck 12, now upside down, can transfer the cap to the cap carrier 24 by gravity, for example. In various embodiments, the cap carrier 24 and the cap can then engage a capping machine conveyor 88 and to travel towards the capping machine 26.

In various embodiments, referring to FIG. 1, the capping machine 26 can include a plurality of chucks 90 extending therefrom where each chuck can be movable between a first position and a second cap-engaging position. In at least one embodiment, each chuck 90 can include a shaft 91 and a cap-engaging portion 92 having a cavity defined therein and configured to engage and retain a cap. In various embodiments, as the cap carriers 24 are conveyed under the chucks 90, the chucks can move from the first position, proximally towards the cap carrier 24, to the second cap-engaging position. In such an embodiment, the chucks 90 can remove the cap from the cap carrier and situate the cap within the cavity of the chuck 90. In at least one embodiment, after the cap is engaged with the chuck 90, the chuck can be configured to move distally from the cap carrier 24 and return to the first position. In various embodiments, the capping machine 26 can then position the chuck 90 such that it can engage the cap with the cap-receiving portion of the container, for example. In at least one embodiment, the chuck 90 can place, snap-fit, friction-fit, and/or screw the cap onto the cap-receiving portion of the container, for example. In other various embodiments, the capping machine can include any suitable capping machine configured to engage and position the cap onto the cap-receiving portion of the container. In various embodiments, after the caps are removed from the cap carriers 24, the cap carriers can be conveyed back to the cap carrier dispenser 78 (FIG. 1) for redeployment onto the top surfaces 20 of at least some of the pucks 12.

In various embodiments, the puck inserts 44, described above, can be created using computerized modeling and a selective laser sintering process, for example. In at least one embodiment, referring to FIGS. 17-20, a 3-dimensional computerized model 95 of the mold 96 can be created using a computerized modeling program, such as AutoCAD® and/or Solid Works®, for example. In such an embodiment, the computerized modeling program can be used to easily and rapidly modify the shape, size, and/or geometry of the puck insert 44 and/or a cavity defined in a top surface of the puck insert 44. In various embodiments, the program can further be configured to electronically model a cap being situated and/or oriented within the cavity of the puck insert 44 to provide feedback information to a computer operator related to a particular configuration, shape, and/or type of cavity prior to the physical creation of the puck insert 44. In at least one embodiment, an operator can use the feedback information to modify the puck insert 44 and/or cavity in the puck insert prior to creating the mold 96 thereby making the puck insert creation process cost-effective and efficient. In various embodiments, the computerized model 95 can include a model of the mold 96.

As outlined above, in various embodiments, the computerized model 95 (FIG. 17) can be used to create the physical mold 96 (FIG. 18) of the puck insert 44. In at least one embodiment, the creation of the mold 96 can include a process known as selective laser sintering, for example. In such an embodiment, the process can include a rapid manufacturing technique which can use a high power laser, such as a carbon dioxide laser, for example, to fuse small particles of plastic, metal, and/or ceramic powders into a mass representing a desired 3-dimensional mold. In various embodiments, the laser can selectively fuse powdered material on a surface of a powder bed by scanning layers of the cross-sections generated from the 3-dimensional computerized model. In at least one embodiment, after each layer of cross-section of the computerized model is scanned, the powder bed can be lowered by one layer of thickness, and a new layer of material can be applied on top of the formed layer. In such an embodiment, the process can be repeated until the mold 96 is completed. In various embodiments, any other suitable method of creating a mold from a computerized model can be used. In other various embodiments, molds can be created without the use of the computerized modeling described above.

Further to the above, in various embodiments, the formed mold 96 can include a top surface forming portion 97 and a cavity forming portion 98 defined in the top surface forming portion. In at least one embodiment, a blank (not illustrated) can be configured to be positioned on the top surface forming portion 97 of the mold 96. In such an embodiment, the blank can be comprised of a thermoplastic sheet or film, and/or any other suitable material. In various embodiments, the blank can be heated to any suitable forming temperature using one or more heaters, such as infrared and/or natural gas heaters, for example. In at least one embodiment, the blank can then be stretched over and/or onto the mold 96 such that the blank can form to the shape of the mold owing to pressure being supplied to the environment surrounding the mold. In such an embodiment, the mold 96 can be temperature-controlled and can be comprised of material such as cast and/or machined aluminum, for example. In various embodiments, the blank can be held against the mold 96 until the blank is cooled. In at least one embodiment, any excess material from the blank can be removed by trimming around the edges of the mold 96. In such an embodiment, the formed blank, now a puck insert, can then be removed from the mold 96 and can include a top surface 100 formed by the top surface forming portion 97 and a cavity 102 formed by the cavity forming portion 98. In various embodiments, the cavity 102 can be configured to receive and/or orient a cap therein. In at least one embodiment, the formed puck insert 44 can be attached to the puck carrier configured to be engaged with the sort conveyor 14, for example.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of sorting and orienting caps, the method comprising:
   a. providing a plurality of pucks to a conveyor, each puck comprising a surface and a cavity defined in the surface;
   b. providing a plurality of caps to the surfaces of at least a portion of the plurality of pucks, wherein the number of the plurality of caps exceeds the number of the cavities in the portion of the plurality of pucks;
   c. settling a group of the plurality of caps into at least some of the cavities in the portion of the plurality of pucks;
   d. removing excess caps by blowing the excess caps with air;
   e. vibrating the portion of the plurality of pucks to cause at least a portion of the settled caps to orient uniformly wherein the vibrating the portion of the plurality of pucks comprises applying one of horizontal vibration, vertical vibration, and combinations thereof;

f. detecting one of proper orientation and improper orientation of the settled caps; and g. transferring the properly oriented caps to a capping machine.

2. The method of claim 1, comprising:

a. positioning the plurality of pucks in a row on a belt portion of the conveyor; and activating the conveyor.

3. The method of claim 1, comprising:

a. integrally forming the plurality of pucks with a belt portion of the conveyor; and activating the conveyor.

4. The method of claim 1, comprising:

a. transferring the settled caps to a plurality of cap carriers when detecting the proper orientation, and b. conveying the plurality of cap carriers and the settled caps to a capping machine.

5. The method of claim 1, wherein the uniformly oriented caps are positioned at a local minimum state of potential energy.

* * * * *